(12) United States Patent
Marshall et al.

(10) Patent No.: US 6,479,052 B1
(45) Date of Patent: Nov. 12, 2002

(54) SPRAY DELIVERY OF CELLS

(75) Inventors: Julian M. Marshall, Headington (GB); Ian Grant, East Grinstead (GB); Stewart A. Cederholm-Williams, Oxford (GB)

(73) Assignee: Bristol-Myers Squibb Company, Skillman, NJ (US)

( * ) Notice: Subject to any disclaimer, the term of this patent is extended or adjusted under 35 U.S.C. 154(b) by 0 days.

(21) Appl. No.: 09/453,256

(22) Filed: Dec. 2, 1999

Related U.S. Application Data

(60) Provisional application No. 60/110,614, filed on Dec. 2, 1998, and provisional application No. 60/155,403, filed on Sep. 22, 1999.

(51) Int. Cl.$^7$ .................................................. C12N 5/00
(52) U.S. Cl. ...................... 424/93.7; 424/529; 424/530; 514/2; 514/21
(58) Field of Search ............................... 424/93.7, 529, 424/530; 514/2, 21

(56) References Cited

U.S. PATENT DOCUMENTS

| | | | |
|---|---|---|---|
| 5,795,571 A | | 8/1998 | Cederholm-Williams 424/94.64 |
| 5,804,428 A | * | 9/1998 | Edwardson et al. ........ 435/212 |

FOREIGN PATENT DOCUMENTS

| WO | WO-9820931 | * | 5/1998 |
|---|---|---|---|

OTHER PUBLICATIONS

Rennekampff, et al., J. Surgical Res., 82 (1996), 288–295, Current Concepts in the Development of Cultured Skin Replacements.

Kaiser, et al., Burns, 20:1 (1994), 23–29, Cultured Autologous Keratinocytes in Fibrin Glue Suspension, Exclusively and Combined with STS–allograft (preliminary clinical and histological report of a new technique).

Hunyadi, et al., J. Dermatol. Surg. Oncol., 14:1 (1988), 75–78, Keratinocyte Grafting: A New Means of Transplantation for Full–Thickness Wounds.

* cited by examiner

Primary Examiner—Jean C. Witz
(74) Attorney, Agent, or Firm—John M. Kilcoyne

(57) ABSTRACT

Provided is, among other things, a method of adhering cells to a target surface which is a tissue surface of a mammal or such a tissue surface coated with a biodegradable polymer sheet, comprising: coating the target surface with a mixture of a first component comprising a non-polymeric fibrin-related protein and a second component effective for converting the fibrin-related protein to fibrin polymer; and spraying a suspension of the cells onto the coated target surface, wherein the mixed two components have formed a fibrin polymer with a tack effective to adhere the cells.

11 Claims, No Drawings

SPRAY DELIVERY OF CELLS

The present application claims the priority of Serial No. 60/110,614, filed Dec. 2, 1998, and Serial No. 60/155,403, filed Sep. 22, 1999.

The present invention relates to methods of delivering and adhering cells to tissue.

In treating damaged skin, such as skin damaged by thermal or chronic wounds, or other wounds, one approach has been to culture keratinocytes derived from biopsies, typically autologous biopsies, until a multilayered, skin-like sheet can be lifted from the culture plate by protease digestion. The difficulties with this process include that the time required to grow such super-confluent cultures, or "epithelial sheet grafts" is of the order of three weeks, the thin sheets are difficult to handle, and the "take," i.e., stable adherence, of the sheet grafts to the basal tissue of the injury has proved problematic. See, e.g., Rennekampff et al., *J. Surg Res.* 62:288–295, 1996. Moreover, keratinocytes grown to such high density take on the character of non-proliferating, differentiated cells, rather than the actively growing cells that contribute to wound healing. See, e.g., Rennekampff et al. A number of approaches have been undertaken to introduce cultured keratinocytes, to wounds while such cells are in a more active growth phase, as reviewed in Rennekampff et al. These have included growing the cells to subconfluence on porous polymeric supports, and applying the supports, inverted to orientate the cells downwards, onto the wounds. Moreover, certain workers in this field have experimented with mixing keratinocytes with fibrinogen, then mixing in thrombin just prior to application to the wound, so that the fibrinogen is converted to fibrin, which forms a polymeric matrix for the keratinocytes. See, Hundyadi et al., *J. Dermatol. Surg. Oncol.* 14:75–78, 1988; Kaiser et al., *Burns* 20:23–29, 1994. The enzymatic conversion of fibrinogen provides ample time during which the composition has a workable tack, allowing the cell-containing composition to be spread over the wound. The fibrin "glue" can also be used to secure a protective layer of allogeneic cadaver skin.

Previous work by the Applicants, together with others working with Applicants, has identified an effective sealant that delivers fibrin, in a "fibrin monomer" form that is stabilized against polymerization, to the site that is to be sealed. At the site, the stabilization conditions are reversed, and an effective clot forms. See, Edwardson et al., European Patent Application No. EP 592,242. One ot the particular advantages of tlhis fibrin monomler sealant of EP5 592,242 is that the sealant can be rapidly prepared from a small amount of a patient's blood only minutes before surgery (or, using manual preparation, within an hour) and this can be done using standard laboratory equipment. Specialized tools for preparing fibrin moniomoier have also been described, and these tools allow an autologous sealant to be prepared from a patient in a rapid, highly reproducible, highly reliable, and highly sate mannier. See, Holm, "Centriftige Reagent Delivery System", WO 96/16713, Holm et al., "Method and Device for Separating Fibrin I from Blood Plasma", WO 96/16714 and Holm, "Centrifuge with Annular Filter", WO 96/16715. The solubilized fibrin monomer composition can be used as a sealant as described in Edwardson et al., EP 592,242. These improvements thus allow for an autologous sealant to be prepared in a rapid, automated process, and the autologous sealant so prepared is free of extrinsic proteinase enzymes such as bovine thrombin or bovine proteins such as aprotinin.

Another fibrin sealant that can be induced to polymerize without the use of a proteolytic enzyme uses (1) a first component of a fibrin analog where the C-terminal region of the γ-chain is sufficiently altered to disrupt self-polymerization and (2) a second component of a fibrin-related molecule such a fibrinogen. See, Cederholm-Williams, WO 9529686A1. On combination of the two components, the fibrin analog polymerizes with the fibrin-related molecule.

Applicants have now shown that keratinocytes sprayed onto a wound site at about the same time frame as the spraying and mixing of two-component fibrin polymer forming systems onto the wound is effective to secure keratinocytes (and, in some cases, fibroblasts) to the wound within a three dimensional fibrin polymer matrix, where the amount of secured cells is effective to expand to form an epithelial layer. In preferred aspects of their invention, the keratinocytes are sprayed concurrently with the spraying and in-flight mixing of a two-component system that renders the fibrin-related molecules of the mixture dynamically competent to polymerize.

The invention also applies to other types of cells that can be secured to a tissue surface, for example to generate new tissue growth or establish the presence of the cells for a sufficient amount of time to achieve a desired result. The invention further relates to spraying cells onto a tissue substrate without fibrin, or with other biocompatible, preferably biodegradable, adhesive polymers. The invention further relates to cells delivered with collagen, with or without fibrin.

SUMMARY OF THE INVENTION

The invention provides, among other things, a method of adhering cells to a target surface which is a tissue surface ot a mammal or such a tissue surface coated with a biodegradable polymer sheet, comprising: coating the target surface with a mixture of a first component comprising a non-polymeric fibrin-related protein and a second component effective for converting the fibrin-related protein to fibrin polymer; and spraying a suspension of the cells onto the coated target surface, wherein the mixed two components have formed a fibrin polymer with a tack effective to adhere the cells. Preferably, the fibrin polymer forms in an amount effective to secure a colonization promoting effective amount of the cells on the target surface. In one embodiment, the method further comprises mixing a cell-adherence promoting effective amount of collagen into the mixture. Preferably, the mixture is sprayed to coat the target surface. The mixture and the suspension of cells can be sprayed concurrently to coat the target surface. Preferably, a colonization promoting effective amount of the cells is entrapped in a three-dimensional matrix of fibrin polymer at the target surface.

The method can comprise adhering the biodegradable polymer sheet to the tissue surface, such that the cell suspension is sprayed onto the polymer sheet, which defines the target surface. In one embodiment, the polymer sheet is adhered together with a removable, external backing layer adapted to further restrict, without eliminating, vapor transport from the tissue, and the method further comprises: removing the backing layer after the polymer sheet has adhered to the tissue and thereafter applying the cell suspension. The polymer sheet can, without limitation, comprise a glucosaminglycan polymer sheet or a cross-linked collagen polymer sheet.

The method can further comprise: culturing autologous cells from a biopsy, taken from the mammal, of a tissue of a given type; and forming the cell suspension from the cultured cells, wherein the tissue to which the cells are applied is of the given type or adjacent to tissue of the given type.

In one preferred aspect of the invention, the tissue is a wound and the cell suspension comprises keratinocytes. Preferably, the cultured keratinocytes of the passage producing the cells for the cell suspension are harvested prior to reaching confluence. The method can further comprise: spraying a suspension of the fibroblasts onto the wound coated with the mixed two components. The fibroblasts can be applied to the same mix creating a fibrin polymer, to a separate mix creating the polymer.

In one embodiment, the first component comprises acid-solubilized fibrin, and the second component can comprise an amount of base effective to sufficiently neutralize the mixture to allow the fibrin to polymerize. The application of the first and second components (of any type) can comprise spraying the first and second components such that a stream of the first component merges with a stream of the second component in flight from a spraying device to the surface. The method can comprise spraying the cell suspension, first component and second component such that streams of the cell suspension, first component and second component merge in flight (from a spraying device to the surface).

In one embodiment, the invention provides a method of, in a mammal, delivering cells to a tissue surface, comprising: spraying a suspension of the cells onto the surface in an amount effective to secure a colonization promoting effective amount of the cells on the surface; and maintaining or growing the cells on the surface. Preferably, the cells are sprayed with liquid flows less than 3.0 ml/min. Preferably, the cells are sprayed onto a tissue surface coated with cell-adherence promoting effective amount of collagen, or the cells are sprayed in an gas stream.

DEFINITIONS

The following terms shall have, for the purposes of this application, the respective meaning set forth below.

bioactive agent. A bioactive agent is a substance such as a chemical that can act on a cell, virus, tissue, organ or organism, including but not limited to drugs (i.e., pharmaceuticals) or hormones (e.g., growth factors) to create a change in the functioning of the cell, virus, organ or organism. Preferably, the organism is a mammal, more preferably a human.

cell-adherence promoting effective amount of collagen. A cell-adherence promoting effective amount of collagen is an amount that reduces the amount of cells needed for a colonization promoting effective amount of the cells or the tissue-growth promoting effective amount of the cells.

colonization promoting effective amount of the cells. A colonization promoting effective amount of adherent cells is an amount effective to lead to the formation of colonies, or to lead to a residence of the cells effective to cause a physiological change in the animal (as when the adherent cells are recombinant cells producing and exporting a biologically active recombinant agent), or to lead to the formation of new tissue.

dynamic fibrin systems. Dynamic fibrin systems are binary fibrin polymer-forming systems that generate, on mixing of the two components, fibrin-related molecules that are dynamically competent to polymerize.

dynamically competent to polymerize. The recital that fibrin-related molecules of a mixture are dynamically competent to polymerize indicates that any barrier to polymerization competence are purely a function of mixing dynamics or, rapid first order kinetics for any tertiary structural changes resulting from the changed conditions, such as pH, of the mixture.

fibrin-related protein. A fibrin-related protein is based on the two pairs of fibrin α-chains, two pairs of fibrin β-chains and two pairs of fibrin γ-chains found in fibrins or fibrinogen. A fibrin-related protein is, or can be readily converted to, a form that is dynamically competent to polymerize. As noted elsewhere in this document, a number of forms of fibrinogen-derived or based molecules can be used to make a fibrin polymer, and are hence fibrin-related proteins.

tissue-growth promoting effective amount of the cells. A tissue-growth promoting effective amount of adherent cells is a colonization promoting effective amount that leads to the formation of new tissue.

DETAILED DESCRIPTION OF THE INVENTION

The cells are sprayed onto a tissue substrate where the fibrin gel-forming components have been sprayed sufficiently recently that the fibrin polymer has not matured too much to have sufficient tack to adhere the sprayed cells. Preferably, the fibrin-related components have matured to a sufficient gel to be more adhesive than either of the two component compositions mixed to form the gel. Most preferably, the two components and the cells are sprayed concurrently, meaning that both the sealant spraying device and the cell suspension spraying device operate at the same time, with the streams directed toward the same tissue.

Preferably, the formation of fibrin that is dynamically competent to polymerize is independent of any proteolytic conversions of fibrin-related molecules. A rapid rate of fibrin polymerization is an important aspect that provides a distinct advantage over fibrinogen/thrombin/cell mixtures. Rapid polymerization allows the rapid application of a thin layer of fibrin and cells to essentially any body surface or cavity. Approaches that provide insufficient initial adhesiveness can experience problems with "run off" from non-horizontal surfaces.

The studies reported herein use the method of the invention as a vehicle to seed wounds with actively growing mono-dispersed keratinocyte suspensions using two spray devices affixed together to spray cells and fibrin sealant towards small experimental wounds. The total number and viability of cells delivered in this way has been estimated in vitro and in vivo and some degree of cell loss is believed to occur. The losses detected may be loss of fragile cells approaching natural senescence or the losses may be due to the spray application system not being optimized for delivery of cells. For example, variations in the air stream has been shown to have a significant effect.

Cell Types: Tissue Types

Cells to be introduced onto a tissue substrate according to the invention include, without limitation, keratinocytes, fibroblasts, hepatocytes, pancreatic cells, lung cells, muscle cells (smooth, cardiac, striated), chondrocytes, osteoblasts, endothelial cells, fertilized ova, adrenal cells and neurones. The cells can be applied according to the invention to supplement or establish the growth of the tissue. Typically, the cells are applied to a tissue substrate appropriately located for the desired tissue growth. The applied cells can include cells transformed in vitro or in situ to a modified phenotype, such as cells transformed to produce a useful bioactive agent, or cells of a given tissue transformed to ameliorate a genetic defect. In this latter case, the desired result can be achieved by at least some residence of the transformed cells at the substrate tissue to which they are adhered. For example, the cells can be sprayed, such as through an endoscopic device, onto lung tissue to provide a therapeutic production of a bioactive agent for a period of time. For cells transformed by incorporation of an appropriate vector in situ the fibrin can act as a transformation enhancing reagent, as discussed in U.S. Ser. No. 60/089,543. filed Jun. 17, 1998, and U.S. Ser. No. 09/334,325, filed Jun. 16, 1999.

Tissues to which the cells are adhered include, without limitation, the basal structure of a wound (which depending on wound depth can comprise the basal epidermal tissue, dermis or muscle fascia), lung, liver, peritoneum or myocardium. The presence of a wound in the tissue epithelium provides a preferred substrate.

In one embodiment of the present invention, an appropriate suspension of fibroblasts, which fibroblasts are preferably autologous, is spray delivered to a wound in conjunction with the spray delivery of the keratinocytes. The fibroblasts then accelerate the formation of a dermal layer to provide better adherent support for the newly forming epidermal layer.

Cells can be directly derived from donor tissue, such as biopsies or blood, or cultured ex-vivo.

In one preferred aspect of the invention, (a) the primary sprayed cells include (or comprise) cells recombinantly transformed to express a bioactive agent, such as a growth factor, helpful to establishing the growth or maintenance of the primary cells, or (b) secondary cells so transformed are added to the primary sprayed cells. The recombinant cells can be stable transformants, meaning that the new characteristic is stably maintained either with or without selective conditions. Such stable transformants can be expected to maintain the recombinant expression phenotype over an extended period of time. Or, the recombinant cells can be transient transformants that can be expected to lose the expression phenotype over a few generations or less. Such transiently transformed cells can be created by co-applying, to the tissue target, an appropriate transformation-inducing vector with the primary cells. In certain embodiments, the recombinantly induced expression of the bioactive agent is most desirable early after application of the cells to the tissue target, at the time during which the cells are least supported by blood supplies or other support mechanisms of the host animal. Thus, transiently transformed cells, or transformed cells that can be expected to have limited viability at the tissue target site, can be usefully employed to provide early expression of suitable bioactive agents.

Two-Component Fibrin Systems

The invention can be used in conjunction with any two component system that combines to form a fibrin polymer. Such two component systems include traditional fibrin sealants where fibrinogen is mixed with a converting enzyme (i.e., an enzyme effective to remove a sufficient amount of ribrinopeptides to create effective fibrin). Such systems are described. for example, in Iilidyadi et al., *J. Dermatol. Surg. Oncol.* 14:75–78, 1988 and Kaiser et al., *Burns* 20:23–29, 1994. More preferred are systems where the only barrier to polymerization are a reversible change in physical form of the fibrin or the separation of two components that are effective to form a binary fibrin polymer. These systems create, on mixing, fibrin that is "dynamically competent to polymerize", as defined above, and can be termed "dynamic fibrin systems." In these systems, the two components can be mixed in flight during spraying to rapidly form a polymer such that a viscous, cell-securing composition is sprayed onto the recipient tissue.

More preferred is the use of a first component that is fibrin (preferably fibrin I) dissolved in relatively mild acid and a second component that is a sufficient amount of base to neutralize the first component, such that mixing the two components thereby converts the fibrin into a polymerization competent form (i.e., dynamically competent to polymerize)., This type of two component system can be manufactured rapidly from autologous blood. The fibrin component carries sufficient prothrombin and factor XIII so that provision of calcium ion in the second component is effective to activate thrombin, thereby initiating maturation of the fibrin to fibrin II and activation of factor XIII to provide fibrin crosslinking.

Specialized tools for preparing such solubilized fibrin, or "fibrin monomer," have been described, and these tools allow an autologous sealant to be prepared from a patient in a rapid, highly reproducible, highly reliable, and highly safe manner. See, Holm, "Centrifuge Reagent Delivery System", WO 96/16713, Rolm et al., "Method and Device for Separating Fibrin I from Blood Plasma", WO 96/16714 and Holm, "Centrifuge with Annular Filter", WO 96/16715. These patent applications describe a molded apparatus that operates in a centrifuge. A first chamber of the apparatus is filled with blood, and a centrifugation process separates the plasma from a pelleted cellular blood fraction. The plasma is transferred to a second chamber into which a conversion enzyme, which is covalently bound to biotin, is inserted. The enzyme operates to convert the fibrinogen in the plasma to fibrin, which fibrin molecules bond to one another to form polymers that precipitate to form a solid. The fibrin precipitate is pelleted by centrifugation, and the remaining plasma is transferred back to the first chamber. The pelleted fibrin precipitate is dissolved with a solubilizinig liquid, which is most often an aqueous solution butTerle at an acidic pH. Tile viscous fibrin monomer solution is mixed with agarose beads having bound avidin to remove traces of biotinylated conversion enzyme, and then washed into a third chamber (or example, a syringe) through a filter that removes the agarose beads. The retained agarose contains any residual enzyme bound via the high-affinity avidin-biotin interaction.

In one preferred aspect, the fibrin composition is enriched in appropriate growth factors, such as fibroblast growth factors or platelet derived growth factors. In another aspect, the cells are co-delivered with platelets or macrophages, or other blood-derived cells. Preferably, such co-delivered cells are autologous.

It should be noted that while autologous sources of fibrin, keratinocytes, or other cells are preferred, other sources are often appropriate. Such sources include fresh frozen plasma (autologous, single donor etc.) or blood bank whole blood.

The compositions delivering fibrin-related proteins preferably further include associated proteins. For example, fibronectin is preferably present in an amount of 3 $\mu$g/ml to 1000 $\mu$g/ml or more, more preferably 30 $\mu$g/ml to 60 $\mu$g/ml or more. Prothrombin is preferably present, on a weight or activity to volume basis, in an amount of 100% or more, more preferably 30–60% or more, where the percent amount is related to the original plasma concentration of prothrombin. Factor XIII is preferably present in an amount of 20–2000% or more, more preferably 200–1000% or more, where the percent amount is related to the original plasma concentration of Factor XIII.

Polymeric Supports

In some contexts, particularly wound care, it can be desirable to provide a coating of a biodegradable polymer that allows the adherence and infiltration of desired cells. Polyurethane membrane dressings useful as such coatings include Hydroderm™ (Wilshire Medical, Inc., Dallas, Tex.) and Spyrofilm™ (Polymedica Inc., Denver, Colo.), which are supplied with a biocompatible adhesive coating. Hyaluronic acid-based membranes useful as such coatings include Laserskin™ (Fidia Advanced Biopolymers, Abano Termre, Italy).

Further useful such coatings include: EpiGen™ polymer membrane (T. J. Smith & Nephew, Limited, HU3 2BN ENGLAND); Apligraft™ support (See, Eaglstein et al., "Tissue Engineering and Development of Apligraft in a Human Skin Equivalent," *Clinical Therapeutics* 19:894–905, 1997; marketing by Novaitis AG), where Apligraft™ is a fibrin-based support incorporating composed of living epidermis and dermis cells; and BioSeed™ support (See, Horch et al., "Fibrin Glue and a Carrier for Cultured Human Keratinocyte Suspensions versus Epidermal Skin Grafts," Abstract, 1997 Annual Meeting, American Institute of Chemical Engineering, Paper 52H).

Useful such polymer coatings also include Integra® artificial skin (Integra Life Sciences, Plainsboro, N.J.). Integra® artificial skin is a bilayer membrane system tor dermis replacement. A dermal replacement layer is made of a porous matrix of fibers of cross-linked bovine tendon collagen and a glycosaminoglycan (chondroitin-6-sulfate). The porous matrix is manufactured with a controlled porosity and defined degradation rate. A temporary epidermal substitute layer is made of synthetic polysiloxane polymer (silicone) and functions to control moisture loss from the wound. The collagen-containing dermal replacement layer serves as a matrix for the infiltration of fibroblasts, macrophages, lymphocytes, and capillaries derived from the wound bed. As healing progresses an collagen matrix is deposited by fibroblasts; simultaneously, the dermal layer of Integra® artificial skin is degraded. See, Burke et al., *Annals of Surgery* 194: 413–427, 1981.

Note that this invention is illustrated with the use of a membrane support coating, but such a support is not required. In the context of wound care, such a support can aid in providing a barrier, such as to vapor transport. However, other methods of providing wound care while epidermal tissue is formed (with the method of the invention) are available. For example, allogeneic skin grafts, such as split thickness skin grafts, can be applied over the sprayed cells to provide a protective layer. The fibrin glue in this context further serves to secure the skin graft. Such grafts are typically glycerolized in the case of allografted de-epithelialized dermis or split skin grafts.

Thus, the invention provides an alternative to forming an epidermis on Integra dermal replacement, use of split skin grafts, cultured epithelial autografts, and the like.

Spraying Devices

A two component fibrin system can be sprayed by any manner of devices known in the art. Typically, mixing should occur immediately before, during or immediately after spraying. Mixing occurring immediately before spraying must be done sufficiently near in time to the spraying event so that viscosity has not increased sufficiently to interfere with the formation of droplets. In the case of dynamic fibrin systems, such prior mixing, except of short duration, is not preferred due to the rapidity with which viscosity increases.

A preferred spraying apparatus would mix the two components of the fibrin system in flight during the spraying operation. In such a system, the kinetics of mixing two streams provides substantial mixing dynamics. Further mixing dynamics can be created by the kinetic energy changes upon collision of the merged streams with the target tissue.

One device is described in Holom, U.S. Pat. No. 5,605,541. The Holm device has a central gas outlet, and two ring outlets arrayed around the gas outlet. File inner ring outlet preferably delivers neutralizing buffer, while the outer ring outlet delivers the fibrin component. The central gas outlet helps shape and merge the output streams. A second spray device can be aligned with the first so that both cells and fibrin are delivered to the target tissue. The Holm device can further be modified to provide a third outlet, such as a ring outlet, for the cell suspension.

Particularly preferred spray devices are described in WO 97/20585 and WO 98/20931. The spray devices described in these patent applications comprise multi-lumen tubes with lumen diameters typically 300 $\mu$m or less. The lumens outlet to a flat surface. With three lumens, at the outlet the lumens preferably align along a straight line. For example, one outer lumen can be used to deliver air or another gas, the middle lumen used to deliver fibrin monomer, and the other outer lumen used to deliver the lower volume base solution. Preferably, the liquid outlets have diameter less that 250 microns, such as 25 to 150 microns or 50 to 125 microns, while the gas outlet is preferably 20 to 50% larger. For example, the outlets can be aligned along a straight line with a 150 micron gas outlet followed by two 100 micron liquid outlets. Preferably, combined liquid flows are less than 3.0 ml/min, such as 0.5 to 0.7 ml/min. The liquid outlets are preferably spaced so that droplets exiting the outlets overlap or contact each other.

Gas flows, when used, are preferably 500 ml/min to 800 ml/min. An adjacent gas flow tends to draw in the liquid stream, and disperse the stream into smaller droplets, creating a "dispersion spray." When gas flow is not used, liquid delivery is in drops or a stream, rather than a dispersion of droplets, such as a conical dispersion. Delivery of liquids by such ejected drops or stream constitutes a form of spraying. Such ejected drops or stream can be preferred where focused application is desired.

When cell suspensions alone are sprayed, the above-described low liquid flow rates are preferably used.

The cell suspension can be delivered from the same spraying device that delivers the two component fibrin system. For example, the embodiment of FIG. 9 of WO 98/2093 1, which has at least three liquid delivery outlets, can be used.

Recombinant Fibrinogen and Fibrin

Genetic engineering can produce fibrinogen and fibrin monomers in comparatively high yields, in substantially pure form, and in the absence of pathogenic viruses such as hepatitis and HIV. Heterologous expression of fibrinogen and fibrin chains also allows the construction of mutations which can mimic naturally occurring fibrin variants, and the isolation and study of these proteins without a need for patients with these rare genetic defects.

Each of the three different polypeptide chains (A$\alpha$, B$\beta$ and $\gamma$) of fibrinogen is coded by a separate gene. The cDNAs for each of these chains have been prepared (Chung et al., *Ann. N.Y. Acad. Sci.* 408:449–456, 1983; Rixen et al., *Biochemistry* 22:3237–3244, 1983; Chung et al., *Biochemistry* 22:3244–3250, 1983; Chung et al., *Biochemistry* 22:3250–3256, 1983) and expressed in prokaryotic organisms. Furthermore, each human fibrinogen chain has been introduced separately (Huang et al., *J. Biol. Chem.* 268:8919–8926, 1993; Roy etal., *J. Biol. Chem.* 267:23151–23158, 1992; Roy et al., *J. Biol. Chem.* 266:4758–4763, 1991) or in combination (Hartwig and Danishefsky, *J. Biol. Chem.* 266:6578–6585, 1991; Huang et al., *J. Biol. Chem.* 268:8919–8926, 1993; Roy et al., 1991, J. Biol. Chem., 266:4758–4763; Redman and Samar, U.S patent application Ser. No. 07/663,380, filed March 1991, available from Natl. Technology Information Service No. PAT-APPL07663 3801NZ) into expression plasmids and transfected into eukaryotic cells.

Most of the plasmids used in expressing recombinant human fibrinogen are derived from those constructed by Dr. D. Chung, University of Washington, Seattle and are based on cDNA clones (Rixen et al., *Biochemistry* 22:3237–3244, 1983; Chung et al., *Biochemistry* 22:3244–3250, 1983; Chung et al., *Biochemistry* 22:3250–3256, 1983). The expression of recombinant fibrinogen chains was first achieved in *E. coli* (Bolyard and Lord, *Gene* 66:183, 1988, Bolyarid and Lord, *Blood,* 73:1202–1206. 1989; Lord and Fowlkes, *Blood,* 73:166–171, 1989). The individually expressed chains show antigenic similarities with fibrinogen and display thrombin cleavable sites similar to those found in native fibrinogenl (Bolyard and Lord, *Blood,* 73:1202–1206, 1989; Lord and Fowlkes. *Blood,* 73:166–171, 1989). Fibrinopeptides A and B can be released from recombinant fibrinogen (Bolyard and Lord, *Blood,* 73:1202–1206, 1989; Lord and Fowlkes, *Blood,* 73:166–171, 1989).

Eukaryotic cells carrying appropriate expression plasmids encoding individual fibrinogen chains have been shown to synthesize the encoded fibrinogen chains and to intracellularly form dimeric chain molecules, e.g. $A\alpha_2$, $B\beta_2$ or $\gamma Y_2$ dimers (Roy et al., *J. Biol. Chem.,* 265:6389–6393, 1990; Zhang and Redman, *J. Biol. Chem.* 267:21727–21732, 1992). Furthermore, when appropriate plasmids containing genes encoding for all three human fibrinogen chains are transferred into the same cell, then not only are all three chains expressed but the polypeptide chains associate in pairs and intact fibrinogen is secreted into the surrounding medium (Roy et al., *J. Biol. Chem.,* 266:4758–4763, 1991; Hartwig and Danishefsky, *J. Biol. Chem.* 266:6578–6585, 1991). Like natural fibrinogen, the secreted recombinant fibrinogen consists of three pairs of distinrct polypeptide c:hains and is functional in forming fibrin polymers.

Fibrinogen is naturally synthesized by liver, and megakaryocyte cells and transformed liver cells maintained in culture are able to continue fibrinogen synthesis and secretion (See Otto et al., *J. Cell. Biol.* 105:1067–1072, 1987; Yu et al., *Thromb. Res.* 46:281–293,1987; Alving et al., *Arch. Biochem. Biophys.* 217:19, 1982). One such cell line is the Hep G2 cells (Drs. Knowles and Aden, Wister Institute, Philadelphia). This line synthesizes an excess of $A\alpha$- and $\gamma$-chains over the Bb-chains resulting in non-productive dimeric complexes of $A\alpha$- and $\gamma$-chains (e.g., $A\alpha 2\gamma 2$). The introduction of an additional expression vector encoding $B\beta$-chains resulted in the formation of trimeric complexes ($A\alpha B\beta\gamma$) which adopt the correct folding and intrachain disulfide bonding patterns (Roy et al., *J. Biol. Chem.,* 265:6389–6393, 1990). The mechanism of this folding is unknown and may involve ancillary proteins and enzymes (Roy et al., *J. Biol. Chem.,* 267:23151–23158, 1992). These studies demonstrated not only the correct transcription of $B\beta$ cDNA but also that the excess $B\beta$-chain enhanced the assembly and secretion of intact fibrinogen.

In Hep G2 cells. the $A\alpha B\beta\gamma$ trimiieiic complexes associate in pairs to form intact fibrinogen molecules, which become glycosylated and are actively secreted from the cell (Huang et al., *J. Biol. Chem.* 268:8919–8926, 1993). Indeed only correctly assembled fibrinogen molecules are secreted. Thus, liep G2 cells have the synthetic and secretory apparatus for the assembly of fibrinogen.

Subsequent experiments halve introduced fibrinogen chain encoding cDNA plasmids into. eukaryotic cells that do not normally synthesize fibrinogen. These experiments successfully produced functional fibrinogen, demonstrating that the factors needed for fibrinogen assembly and secretion are not unique to liver-derived cells like Hep G2. Eukaryotic cells known to be capable of assembling and secreting recombinant fibrinogen include baby hamster kidney cells (BHK), COS cells and Chinese hamster ovary cells (CHO) (Roy et al., *J. Biol. Chem.* 266:4758–4763, 1991; Hartwig and Danishefsky, *J. Biol. Chem.* 266:6578–6585, 1991; Farrell et al., *Biochemistry* 30:9414–9420, 1991).

Intact functional fibrinogen secreted by stably transformed eukaryotic cells results in the accumulation of fibrinogen levels of around $1-\mu 2$ Mg/ml. Methods are known for increasing the output of recombinant proteins from transfected cells like CHO cells such that the expression levels can approach a thousand fold the basal secretory level.

Additional description of methods of recombinantly producing fibrin-related molecules can be found in PCT/US95/05527.

Collagen

The invention also relates to spraying cells onto a tissue surface coated with a cell-adherence promoting effective amount of collagen. Preferably, the collagen is sprayed onto the tissue surface.

Other Adhesive Matrixes

Cells can also be sprayed into other polymeric adhesives or viscosity-enhancing, polymer-based compositions. Preferably, the adhesive or viscosity-enhancing polymer is co-delivered, as with one of the above described multi-outlet spray devices. For example, cells can be delivered with adhesive compositions comprising collagen, hyaluronic acid, or other suitable polymers. In the case of at least certain polymers composed of multiple acidic groups, such as hyaluronic acid, an acidic solution has significantly lower viscosity, such that mixing in conjunction with application of a base solution will increase viscosity. Thus, such polymers can be more conveniently delivered with a mixing process similar to that used with acid-solubilized fibrin.

The following examples further illustrate the present invention, but of course, should not be construed as in any way limiting its scope.

EXAMPLE 1

Preparation of Fibrin Monomer

The biochemical process for preparing fibrin monomer is fully automated and has been previously described (Kjaergard et al Cardiovascular Engineering 2:204–206, 1997). One hundred and twenty mls of the patient's blood is mixed in the preparation set with sodium citrate for anticoagulation. Rapid cycle centrifugation isolates 60 ml of plasma, which is reacted with biotinylated batroxobin for 10 minutes at 37° C. The biotin-batroxobin complex catalyzes the release of fibrinopeptide A from fibrinogen but does not activate factor XIII, resulting in the formation of a fibrin I polymer, which is acid soluble. The fibrin I polymer is isolated by centrifugation and dissolved in 3.5 ml 0.2M sodium acetate buffer (pH 4.0). Avidin, covalently bound to agarose, is added to the solution to complex the biotin-batroxobin to the agarose. The biotin-batroxobin:

avidin-agarose complex is then separated from the fibrin I solution by filtration.

The acidic fibrin I solution is drawn into a vial and transferred to the applicator unit. A syringe within the applicator unit contains 0.75 M carbonate/bicarbonate buffer (pH 10). The two solutions are administered simultaneously and intimately mixed during the application process. Mixing at a 7:1 ratio (fibrin I:buffer) initiates polymerization. At a neutral pH resulting from the mixing, and in the presence of calcium ions supplied by the carbonate/bicarbonate buffer, endogenous pro-thrombin is converted to;thrombin, causing fibrinopeptide B to be cleaved from fibrin I to form fibrin II. Thrombin also activates factor XIII, which acts upon the fibrin II to form a stable fibrin II polymer. In human studies the process is complete in 30 minutes and yields approximately 4.5 mls of concentrated fibrin sealant rich in fibrin associated proteins including fibronectin.

EXAMPLE 2

Cell Growth on Fibrin Polymer

An in-vitro study was performed to assess whether sub-confluent pig keratinocytes were able to use polymerized fibrin sealant (produced using the Example 1 process) as a substrate for adherence and growth. Polymerized fibrin sealant was prepared from samples of fibrin I solution produced from a single donation of pig blood using the Example 1 process. The concentration of fibrin I in the solution was 23.64 mg ml$^{-1}$, and the OH value was 4.43. A single 24 well tissue culture plastic assay plate was used (0.8 cm internal well diameter). The experimental groups are described in the following table:

FIG. 8.1$a$: Groups for iii-vitro Study of Pig Keratinocyte Growth on Fibrin Sealant

| 0.8 cm wells | Group 1, n = 3 | Group 2, n = 3 |
|---|---|---|
| Fibrin clot | 150 μl fibrin I solution<br>750 μl DMEM (10% FCS)<br>50 μl type I collagen solution | 150 μl fibrin 1 solution<br>750 μl DMEM (10% FCS)<br>50 μl 0.02 M acetic acid |
| Cells | 1/10$^5$ passage 2 pig keratinocytes<br>5/10$^4$ irradiated 3T3 feeder cells | 1/10$^5$ passage 2 pig kertatinocytes |

One hundred and fifty micro-liters of fibrin I solution was added to each of 6 wells. Seven hundred and fifty micro-liters of DMEM culture medium (containing 10% FCS), with 50 μl of 50 μg/ml type I rat tail collagen solution (dissolved in 0.02M acetic acid) was added to each of 3 wells in Group 1. For the 3 wells of Group 2, the same solution was added; however the rat-tail collagen solution was omitted and replaced with 50 μl of 0.02 M acetic acid. The fibrin I solution polymerized immediately on addition of the DMEM solution. Fifty thousand irradiated 3T3 feeder cells in 0.5 mls of keratinocyte growth medium were applied to the surface of polymerized fibrin sealant in the 3 wells of Group 1, and 0.5 mls of keratinocyte growth medium alone were applied to wells in Group 2. One hundred thousand (1×10$^5$) passage sub-confluent pig keratinocytes were applied in 0.5 mls of keratinocyte growth medium to the surface of all 6 wells. After 2 days of culture, the medium was changed by gentle aspiration. After 4 days the fibrin sealant clot was still present in the base of each well. After a further change of medium the clot was lifted from the well using a scalpel (size 11 blade) and a pair of toothed forceps.

Each clot was then blocked and frozen in OCT blocking compound. Cryosections of 15 μm thickness were cut transverse and tangentially to the upper surface of the clot. It had been hoped that the latter sections would allow an assessment of the morphology of adherent keratinocytes. Fibrin sealant clot has a much lower strength than tissue biopsies and unfortunately all such sections fragmented during sectioning. The intact transverse cryo-sections were fixed and stained for keratin 14 immuno-reactivity using standard immunocytochemical techniques and fluorescence microscopy. Keratinocytes were visible on the surface of the fibrin sealant clot in both experimental groups.

EXAMPLE 3

Wound Care

Anaesthetic and surgical procedures have been described previously in this well-established wound model (Kangesu et al., Brit. *J. Plastic Surg.* 46:3893–400, 1994). Three circular 4 cm diameter full thickness wounds were made on to the exposed muscle fascia on each flank of the thoracic cage of the Large White Pig. When Integra™ dermal replacement was used in this model, meticulous haemostasis of the wound bed was achieved by careful use of a bipolar diathermy (i.e., generation of heat in tissue by electric currents for medical or surgical purposes). Integra™ dermal replacement was prepared in the manner described by Burke et al. (Artificial Skin, Dermal Regeneration Template, Physician Training Manual, Integra Lifesciences Corporation, 1996), and then cut into 4.5 cm diameter discs which were sutured to the wound base using interrupted 5° monofilament sutures positioned 2 to 3 mm internally to the edge of the disc. The wounds were isolated from the surrounding skin using polytetraflouroeurathane (PTFE) chambers secured in position using 20 silk sutures. The Integra™ dermal replacement was covered with a non-adherent dressing and the chambers filled with lightly compacted saline soaked gauze. A foam lined protective jacket was strapped around the trunk of the animal to prevent any inadvertent damage to the wounds. A skin biopsy to initiate keratinocyte cultures was performed on the same day as the creation of full thickness wounds (isolated by percutaneous chambers) and grafted with Integra™ dermal replacement onto the thoracic trunk fascia.

Blood was collected from the left external jugular vein of the pig. The protocol for the production of autologous fibrin sealant was according to Example 1.

The protocol for grafting Integra™ dermal replacement (or artificial skin) was refined (as detailed in Clayton and Bishop, *J. Burn Care Rehabil.*, vol. 19:(4):358–363, 1998) to achieve consistently high rates of take.

An animal aged 10 weeks were used in this experiment. The protocol used a period of only 10 days between the initial biopsy and application of the cultured cells. (The initial biopsy could thus be taken during the same anaesthetic used to create the isolated wounds and apply the Integra™ artificial skin.). Dressings were changed under general anaesthetic on the 3$^{rd}$ and 8$^{rd}$ days.

On day 10 the animal was anaesthetized and the left external jugular vein cannulated. Approximately 4.5 cm$^3$ of pig fibrin I solution was produced using a single manufacturing run. The wounds were exposed, and the temporary silastic membrane of the Integra™ dermal replacement removed. The take of Integra™ dermal replacement in this experiment was 100% in all of the 6 wounds.

Six large (T75) flasks of keratinocytes at 80–90% confluence were dispersed using 5 mls of pre-warmed 0.05% trypsin/0.02% ethylenediamine tetra-acetic acid (Gibco BRL,. Life Technology) administered to each flask, with the flasks incubated at 37° C. The cells took 10 minutes to detach from the tissue culture plastic. The action of trypsin was neutralized by the addition of serum containing media. Approximately 1.4×10$^6$ viable cells were harvested in total.

The keratinocytes were suspended in keratinocyte growth medium for spraying. Viability was assessed from an unsprayed sample at the end of the spraying procedure.

Approximately 0.6 cm³ of the autologous pig fibrin sealant (approximately 22 mg/ml fibrin monomer) and 0.6 cm³ of porcine cell-suspension were applied to wounds 1–3. Approximately 0.6 cm³ of pig fibrin sealant with porcine keratinocyte growth media without cells were applied to wounds 4–6. The fibrin sealant and carbonatelbicarbonate buffer were sprayed with one spray device, and the cells were sprayed. by a like device taped to the first device. The spay heads were held 2 to 5 cm from the wounds. The device used was according to WO 97/20585, where three linearly aligned 300 μm outlets were used to deliver, respectively, air, acid-dissolved fibrin and carbonate/bicarbonate buffer. Wounds on the left side of the animal were in one experimental group, wounds on the right side of the animal were in another group. This arrangement avoided any potential contamination of the fibrin sealant alone wounds by sprayed keratinocytes from the other experimental group.

The cell density of the cell-suspension was estimated to be $2.78 \times 10^6$ cells cm$^{-3}$.

The total number of cells sprayed per wound was thus estimated to be $1.67 \times 10^6$. The viability of the cell suspension before spraying was estimated to be 92.8%. The fibrin sealant polymerized on the wound surface almost immediately after application.

Earlier studies, performed using second passage (P2) keratinocytes from the same animal had indicated a 63.2 (S.D. 5.4) % viability for cells sprayed on to 5% agarose using the same equipment (in the absence of autologous fibrin sealant). Thus, the total number of viable cells delivered to each wound would be expected to be approximately $1.1 \times 10^6$ (or $\approx 8.8 \times 10^4$ viable cells cm$^{-2}$ wound area).

A sample of the cell suspension (excess to that used on the wounds) was sprayed into a 75 cm² collagen coated tissue culture flask seeded with $2 \times 10^6$ lethally irradiated mouse 3T3 cells. These cells formed a near confluent population within 3 days. This population was subsequently cultured for two further passages with no evident impediment in growth rate compared with unsprayed keratinocytes.

The wounds were photographed and dressed with a layer of non-adherent dressing, and the chambers were filled with moist saline gauze. Punch biopsies were taken from wounds 3 and 4, approximately 5 minutes after application of the two different wound treatments. Further biopsies were taken on the 4$^{th}$ day after the treatment under general anaesthesia, and at day 14 the wounds were harvested at euthanasia.

Day 0: On both wounds a coating layer of fibrin sealant of approximately 60 μm thickness was present. Keratinocytes suspended in the sealant were detectable only in biopsies from wounds having cells applied by spray application, and were of isolated and spherical morphology.

The total number of cells (both viable and non-viable) delivered to each wound was estimated to be approximately $1.7 \times 10^6$, so that the predicted density of sprayed cells on the wounds would be approximately $1.3 \times 10^5$ cm$^{-2}$.

Day 4: Four days after treatment with a sprayed mixture of fibrin sealant and suspended keratinocytes, keratinocyte colonies were detected on or closely proximal to the wound surface. The layer of fibrin sealant was no longer evident. No keratinocytes were detected in the biopsy from the sealant plus medium only control wound.

Day 14: A multi-layered mantle of epithelium was present on the wound surface two weeks after spray application of the fibrin sealant I keratinocyte mixture. No epithelium was present on the surface of the wounds that were treated with a mixture of sprayed fibrin sealant and medium alone.

Epidermal cover at 14 days: Epithelium on the wound surface 14 days after sprayed application of a cultured keratinocytes did not possess a stratum corneum. Macroscopically, epithelium is denoted by a change in the opacity of the wound surface. Reference to biopsies confirmed that areas of epithelium had a mat appearance in comparison with the otherwise glistening surface of the wound.

The mean epidermal cover on wounds 1–3 at 14 days after sprayed application of a mixture of fibrin sealant and keratinocytes, (calculated as a percentage of the total wound area) was 66% as illustrated by the table below. No epithelium was present on wounds 4–6, which were treated with a sprayed mixture of fibrin sealant and medium alone.

TABLE

Epidermal cover.

| Wound | treatment | Epidermal cover 14 days after Grafting keratinocytes, (% total wound area) |
|---|---|---|
| 1 | Fibrin/keratinocyte spray | 74. |
| 2 | Fibrin/keratinocyte spray | 64. |
| 3 | Fibrin/keratinocyte spray | 61. |
|   |   | Wounds 1–3, mean = 66 (SD 5.7) |
| 4 | Fibrin spray | 0 |
| 5 | Fibrin spray | 0 |
| 6 | Fibrin spray | 0 |
|   |   | Wounds 4–6, mean = 0 |

A gradual movement of the Integra™ dermal replacement disc (and hence the wound bed) with respect to the PTFE wound chamber was noted. The movement was presumed to be a consequence of phenomenon of "wound shift" as a result of the animal's growth. A significant fraction of the wound bed at 14 days after treatment was a consequence of wound shift, never subjected to the fibrin sealant/keratinocyte spray. The reconstitution of epidermis calculated as a percentage of sprayed Integra™ artificial skin would be considerably greater than the 66% recorded without taking into consideration the migration phenomenon.

Keratin 6 and Collagen VII Staining

Tissue biopsies were stained for immuno-reactivity to keratin 6 and collagen VII. At day 4 no immuno-reactivity to keratin 6 or collagen VII was detected. At day 14 however supra-basal keratinocytes stained strongly for K6. Collagen VII immuno-reactivity was detectable below areas of epidermis and immediately adjacent to keratinocyte cysts. Collagen VII immuno-reactivity was detected in the form of multiple overlapping streaks rather than a single continuous band. No keratin 6 or collagen VII immuno-reactivity was detectable within biopsies from wounds sprayed with a mixture of fibrin-sealant and medium alone.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the ,preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of adhering keratinocytes to a target surface which is a wound of a mammal coated with a biodegradable polymer sheet comprising:

harvesting keratinocytes from cell culture prior to their reaching confluence;

adhering a biodegradable polymer sheet to the tissue surface that is the target surface;

coating the biodegradable polymer sheet at the target surface with a mixture of a first component comprising a non-polymeric fibrin-related protein and a second component effective for converting the fibrin-related protein to fibrin polymer; and spraying a suspension of the keratinocytes onto the fibrin polymer-coated target surface, wherein the mixed two components have formed a fibrin polymer with a tack effective to adhere the keratinocytes, wherein a colonization promoting effective amount of the cells is secured on the target surface and the fibrin polymer forms in an amount effective to secure a colonization promoting effective amount of the cells on the target surface, and wherein the application of fibrin polymer and fibrin-polymer adhered keratinocytes is effective to provide the formation of epidermal cover at the target surface.

2. The method of claim 1, wherein the biodegradable polymer sheet comprises a porous matrix of fibers of cross-linked bovine tendon collagen. surface.

3. The method of claim 1, wherein the biodegradable polymer sheet comprises a porous matrix of fibers of (a) cross-linked bovine tendon collagen and (b) a glycosaminoglycan.

4. The method of claim 1, further comprising mixing a cell-adherence promoting effective amount of collagen into the mixture.

5. The method of claim 1, wherein the mixture is sprayed to coat the target surface.

6. The method of claim 1, wherein the mixture and the suspension of cells are sprayed concurrently to coat the target surface.

7. A The method of claim 1, wherein a colonization promoting effective amount of the cells is entrapped in a three-dimensional matrix of fibrin polymer at the target surface.

8. The method of claim 1, further comprising:

culturing autologous keratinocytes from a biopsy, taken from the mammal; and forming the cell suspension from the cultured cells.

9. The method of any one of claims 1, 4 through 8, 2 and 3, wherein the first component comprises acid-solubilized fibrin, and the second component comprises an amount of base effective to sufficiently neutralize the mixture to allow the fibrin to polymerize.

10. The method of claim 9, comprising spraying the first and second components such that a stream of the first component merges with a stream of the second component in flight from a spraying device to the surface.

11. The method of claim 9, comprising spraying the cell suspension, first component and second component such that streams of the cell suspension, first component and second component merge in flight from a spraying device to the surface.

* * * * *